United States Patent [19]

Roarty

[11] Patent Number: 4,881,409
[45] Date of Patent: Nov. 21, 1989

[54] MULTI-POINT WALL THICKNESS GAGE
[75] Inventor: David H. Roarty, Murrysville, Pa.
[73] Assignee: Westinghouse Electric Corp., Pittsburgh, Pa.
[21] Appl. No.: 205,891
[22] Filed: Jun. 13, 1988
[51] Int. Cl.[4] .......................................... G01N 29/00
[52] U.S. Cl. ..................................... 73/597; 73/644; 376/252
[58] Field of Search .................. 73/596, 597, 598, 599, 73/600, 628, 637, 641, 644; 376/252

[56] References Cited

U.S. PATENT DOCUMENTS

| | | | |
|---|---|---|---|
| 2,700,895 | 2/1955 | Carson | 73/641 |
| 4,119,938 | 10/1978 | Alais | 340/1 R |
| 4,122,725 | 10/1978 | Thompson | 73/644 |
| 4,232,557 | 11/1980 | Vasile | 73/629 |
| 4,375,166 | 3/1983 | Auphan | 73/628 |
| 4,386,527 | 6/1983 | Maucher | 73/597 |
| 4,448,075 | 5/1984 | Takemura et al. | 73/626 |
| 4,570,486 | 2/1986 | Volkmann | 73/597 |
| 4,642,215 | 2/1987 | Klinvex et al. | 376/249 |
| 4,649,749 | 3/1987 | Hazony et al. | 73/597 |
| 4,715,008 | 12/1987 | Jones | 364/503 |
| 4,716,765 | 1/1988 | Hirama | 73/626 |

FOREIGN PATENT DOCUMENTS

| | | | |
|---|---|---|---|
| 958531 | 3/1950 | France | 73/644 |
| 0586380 | 12/1977 | U.S.S.R. | 73/637 |
| 0655962 | 4/1979 | U.S.S.R. | 73/644 |

OTHER PUBLICATIONS

Prediction and Mitigation of Erosive-Corrosive Wear in Secondary Piping Systems of Nuclear Power Plants, R. G. Keck, P. Griffith, Sep. 1987, NUREG/CR-5007, pp. 1-3, 14-15.

Primary Examiner—Stewart J. Levy
Assistant Examiner—Lawrence G. Fess
Attorney, Agent, or Firm—Michael G. Panian

[57] ABSTRACT

A multi-point wall thickness gage (10) comprises a pad (16) of flexible magnetic material that includes an array of ultrasonic transducers (13) and a multi-point ultrasonic transmitter and receiver (25) to which each transducer (13) is attached. The magnetic pad (16) is attachable to the wall of a ferro-magnetic object (19), and serves to hold the array or matrix of ultrasonic transducers (13) against the wall of the object. The specific region of the object wall being inspected is marked off (17), and the magnetic pad (16) is periodically applied over this region (17). The output of the transducers (13) is used to detect whether any wall thinning is occurring over the particular area of the object covered by the magnetic pad (16), and if so, the particular pattern of thinning within the area. Trend monitoring is simplified since exact relocation of the transducers (13) for periodic measurements is more readily accomplished.

19 Claims, 2 Drawing Sheets

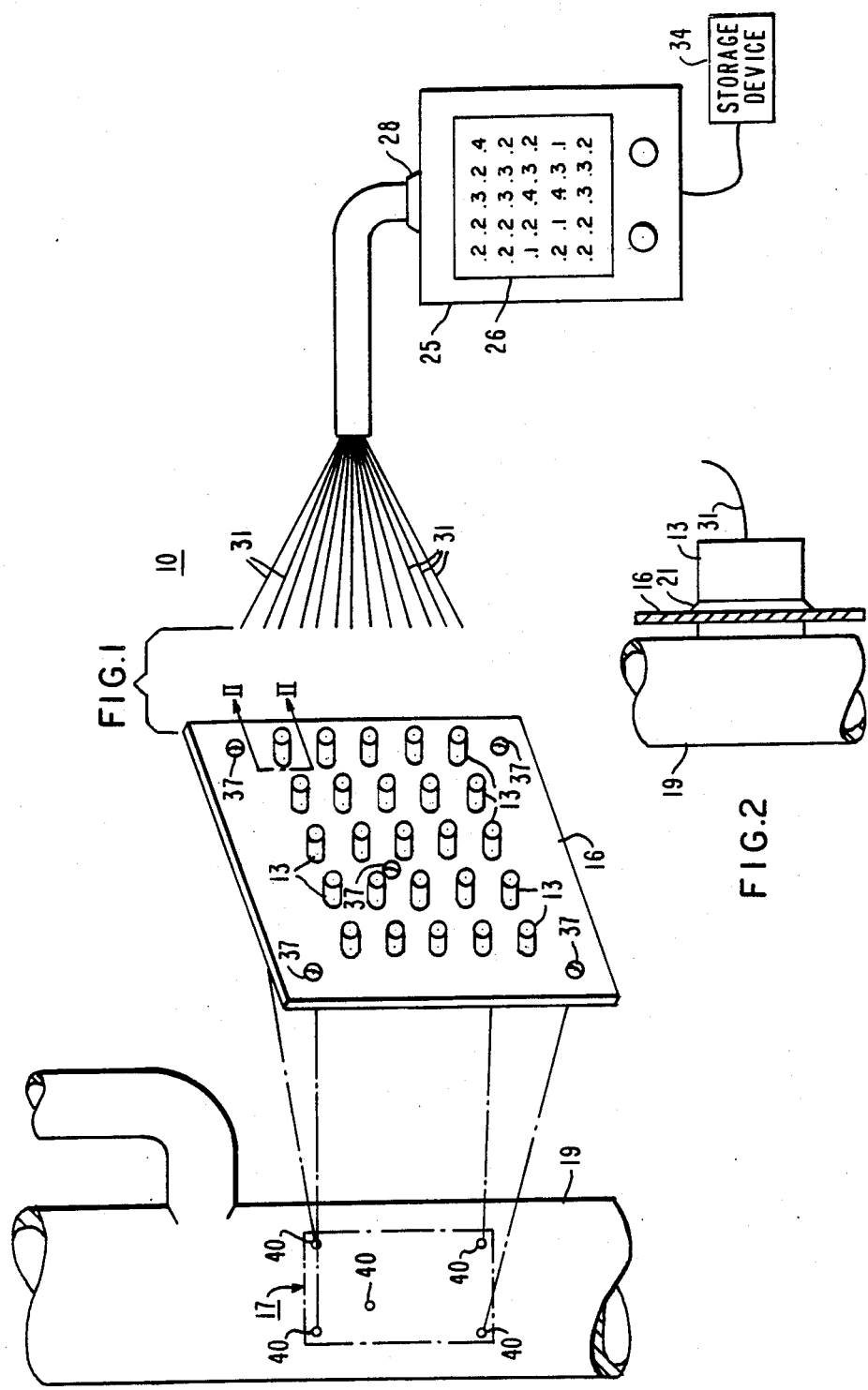

MULTI-POINT WALL THICKNESS GAGE

TECHNICAL FIELD

The invention relates to a method and apparatus for measuring the thickness of structures, and more particularly to a multi-point wall thickness gage for monitoring the wall thickness of ferro-magnetic pipes.

BACKGROUND OF THE INVENTION

In a typical nuclear power plant, operating conditions present unique safety considerations. Foremost of these, is the prevention of any inadvertent release of radiation to the surrounding environment in the unlikely event of equipment malfunction. Additionally, in a system such as a pressurized water reactor (PWR), coolant or water temperatures and pressures can place greater demands on piping as well as other component systems. Typically, a PWR may be operated at temperatures and pressures in the range of about 315° C. (600° F.) and 15.5 MPa (2250 psia), respectively. Such conditions can aggravate high rates of material wear in parts of both primary and secondary piping systems, the latter often referred to as feedwater and extraction steam pipes. Although, not unique to nuclear power plants, such material wear needs to be effectively monitored in order to prevent the possibility of failure of piping systems as a result of material wear. Such failures can cause considerable operational problems, including unscheduled plant shutdowns for emergency pipe replacements or repairs.

Certain phenomena, such as single- and two-phase corrosion/erosion wear of pipes can reduce wall thickness over a given area. This type of wall thinning generally only affects carbon steel pipes which are ferro-magnetic. Experience has shown that such wear is caused by the combined effect of electro-chemical (corrosive) and mechanical (erosive) mechanisms. Under the operating conditions found in secondary piping systems, which are more apt to experience two-phase wear, the steel pipe corrodes, forming a thin layer of iron oxide on the exposed metal surface. Normally, this layer would separate the corrosive environment of the otherwise bare pipe wall from the corroding material and, in the absence of erosive mechanisms, prevent further corrosion of the pipe wall. However, mechanical forces such as fluid turbulence act on the pipe and remove some or all of the oxide layer, thereby removing the protectiveness and allowing the pipe to corrode anew. This cycle of oxide growth and removal continuously wears away the underlying pipe wall material, leading to progressive loss of the pipe's mechanical integrity over extended and lengthy exposure to such wear and can under some conditions ultimately result in the failure of the pipe.

Such wear is found to be dominant in or near bends, tees, and fittings within the piping system. This is because the wear is fundamentally caused by the interactions of the continually flowing liquid in the pipes with the corroded oxide surfaces. In bends, tees and other similar locations, these liquid/material interactions can be more severe and cause relatively more wear. For example, common flow in pipe bends may never be fully developed, which can lead to increased level of local fluid turbulence and greater dissolution of the oxide. Such localization of pipe wall wear can pose a problem with respect to the prediction and correction of pipe wall thinning. Efforts have been made to predict where such pipe wall thinning may tend to occur to help in the deployment of in-service inspection teams to monitor the wear of the carbon steel pipes. One such example of an effort to predict such wear in carbon steel pipes as a function of typical operating conditions within a nuclear power plant, can be found in a Nuclear Regulatory Commission publication entitled "Prediction and Mitigation of Erosive-Corrosive Wear in Secondary Piping Systems of Nuclear Power Plants" by R. G. Keck and P. Griffith, September 1987, referred to as NUREG/CR-A5007.

Even after such areas of localized wear have been identified, it can be difficult to effectively monitor the rate of wear over a given period of time. The rate of wall thinning is typically based on thickness measurement readings taken at different times at the same location and is used in structural integrity life predictions. The use of ultrasonic devices for the measurement of the thickness of a structure to determine its wear is well-known in the art. An example of which is U.S. Pat. No. 4,642,215 issued on Feb. 10, 1987 to Klinvex et al., and assigned to the assignee of the present invention. Moreover, the use of ultrasonic transducers to periodically measure the thickness of a structure over time to monitor that structure so as to prevent its unexpected failure is equally well-known. In nuclear reactor systems such monitoring of vital components of a power plant has increased importance.

In ultrasonic measuring, an ultrasonic beam is sent from a transmitter into the structure to be monitored and a return signal or echo is received by a receiver. The time it takes from transmission to reception is determined, and is converted into a signal indicative of the thickness of the particular structure. Once such a device is calibrated for whatever material is being tested, accurate readings of the structure can be taken.

In measuring secondary piping systems of a nuclear power plant, conventional wall thickness gages require that a grid be painted on the pipe, then measurements are taken point by point. A typical grid may be from 50 to 100 points. This technique can be extremely time consuming and difficult to replicate. A typical pipe may require hundreds of locations to be monitored. With a large number of areas to test, the total number of points to be monitored can be quite numerous, on the order of about one million. In order to perform measurements at a typical location, the following steps typically are carried out. First, insulation must be removed from around the pipe. After a particular location has been identified, the grid must then be painted onto the pipe. However, the grid to be used for testing must first be defined by the technician. With a painted grid, each location must have associated therewith an alphanumeric character in order to identify each particular point. After the grid has thus been identified and defined on the pipe, a point by point analysis, for example, by an ultrasonic transducer, is performed. The readings for each particular point are identified and recorded for future reference.

Such detailed and time consuming preparation for thickness measurement can lead to a high cost for such operations. Also it can be difficult to replicate the exact testing procedure at a later time. During the operation of the plant, it is not uncommon for the painted grid to fade and become undetectable. Thus, for subsequent thickness measurement operations it may be necessary to again identify, define and paint the grid, after first locating the precise location of the previous grid in order to provide for exact replicability of the prior testing. In order to effectively monitor the rate of wall thinning, the subsequent measurements must be taken at the same location. It would be highly desirable to provide a device which would greatly reduce the costly time and procedures now used to provide an indication of pipe wall thickness for a vast number of individual points.

DISCLOSURE OF THE INVENTION

It is therefore an object of the present invention to provide a device to obtain wall thickness measurements over a predetermined area within an easily replicable grid.

It is another object of the present invention to provide a device that will save a tremendous amount of cost for such an inspection by allowing for simultaneous multi-point readings.

It is a further object of the present invention to provide such a device which has a higher degree of reliability of the wall thickness measurement so that fewer re-inspections would be required at the same location.

The above objects are attained by the present invention, according to which, briefly stated, apparatus for simultaneously measuring the thickness of a ferro-magnetic material at a plurality of discrete points comprises a magnetic pad securable to the material at a predetermined location, which includes a plurality of ultrasonic transducers associated therewith so as to form a grid pattern for measuring the thickness of the material at each of the discrete points. Means for simultaneously transmitting an ultrasonic pulse through each the transducers and into the material is included, as well as a means for receiving a plurality of return signals from the material. A separate return signal is received through each of the transducers, the return signals being indicative of the thickness of the material at each of the discrete points.

BRIEF DESCRIPTION OF THE DRAWINGS

The invention will become more apparent by reading the following detailed description in conjunction with the drawings, which are shown by way of example only, wherein:

FIG. 1 is a plan view of the overall device of the present invention;

FIG. 2 is a view taken along the line II—II of FIG. 1;

DESCRIPTION OF THE PREFERRED EMBODIMENT

In a typical nuclear reactor power plant, the piping system can involve pipes which are up to about 91 cm (36 in.) in diameter. Since failure of such a large pipe can given rise to a multitude of complications, it is important to accurately and effectively monitor the wall thickness of such pipes. Thus, the multi-point wall thickness gage of the present invention was developed. The overall device 10, as shown in FIG. 1, includes a plurality of ultrasonic transducers 13 operatively associated with a flexible pad 16. The pad 16 is flexible so that it can be placed in a variety of areas, generally designated at 17, so as to wrap around a cylindrical pipe 19, or at bends/elbows, tees and wyes, etc., thereon. Preferably, the pad 16 is in the form of a rectangular shape; but its actual configuration is dependent upon the area it is to be placed, such as the amount of curvature of an elbow. Preferably, the attachment means, generally designated at 21, for the ultrasonic transducers 13 are quick release fasteners. This would allow for ease of replaceability of the transducers 13 in the event that a transducer should fail and to allow transducers to be transferred among various pads. The transducers are attached to the pad so that they have a proper orientation with respect to the pipe wall, when the flexible pad is secured thereto (see FIG. 2). Each location on the pad 16 is sequentially numbered, as a grid or matrix, and the transducers 13 are numbered accordingly.

Figure 3A:
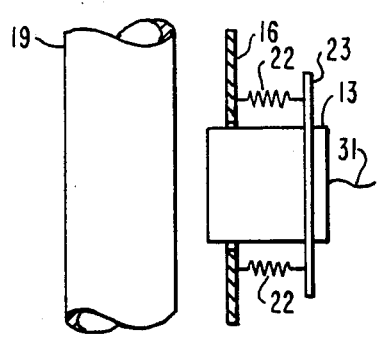
FIGS. 3a and 3b show a flexible attachment means for the transducers.
Figure 3B:
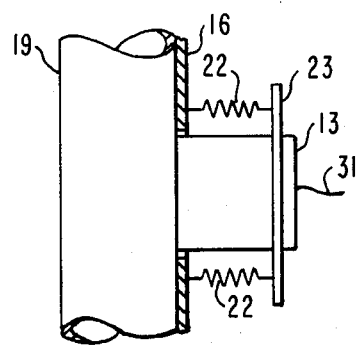

In order to ensure that the transducers 13 maintain complete surface contact with pipe 19 when the pad 16 is attached thereto, the attachment means 21 would have a flexible constraint, such as a spring 22 connected between the pad 16 and a collar 23 on the transducer 13 (see FIG. 3). Prior to contact with the pipe 19, the transducer 13 projects below the surface of the flexible pad 16 (FIG. 3A). As the pad 16 is placed over the pipe 19, the transducers 13 will contact the pipe first. When the pad 16 has been placed flush with pipe 19 (for a secure fit), the transducers 13 will also be flush with the pipe for a good ultrasonic reading (FIG. 3B). By use of the spring 22, the transducer 13 is biased in a direction towards the pipe 13 so that surface contact is maintained between the transducer and the material to be tested.

Figure 4:
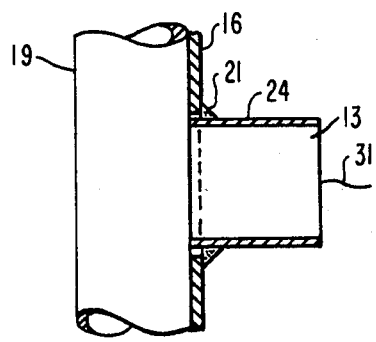
FIG. 4 shows a second means for attaching the transducers to the flexible pad.

Another embodiment of the attachment means 21 is shown in FIG. 4. In this alternative embodiment the transducer 13 has a magnetic housing 24 which can be attached to the flexible pad 16. The bottom surface of the magnetic housing 24 is flush with that of the pad 16. However, the housing 24 (and thus the pad) extend slightly beyond the face of the transducer 13. Thus, when the flexible pad 16 is placed flush with the pipe 19, the transducers 13 will be positioned with respect to the pipe wall a known distance. This air space would preferably be filled with an appropriate couplant. The ultrasonic readings obtained by the transducers can then be calibrated accordingly.

Preferably, the flexible pad 16 is made of a magnetic material since carbon steel pipes 19 are ferromagnetic. In this manner, the magnetic pad 16 is readily securable to the pipe to be measured and requires no other attachment needs. Associated with the transducers 13 is a conventional ultrasonic transmitter and receiver, or transceiver, 25 capable of carrying a multi-channel input and providing a matrix-type readout on the screen 26. The transceiver 25 is in communication with the transducers 13 by a multi-channel port 28 having a plurality of leads 31 corresponding to the number of transducers, such that ultrasonic readings can be simultaneously taken at each of the transducer locations. Preferably the outputs from the transducers 13 are also passed onto a storage device 34 for later retrieval by the thickness gage 10 during subsequent measurements, to provide comparison with previous readings so as to give an indication of the rate of wall thinning over time. Depending on how the ultrasonic transducers 13 are attached to the pad 16, its thickness is preferably on the order of 2-3 mm (0.08 to 0.12 in.). If the transducers 13 are somewhat permanently attached to the pad, such as by epoxy or riveting, it can be relatively thin. To provide for the quick release fasteners, the flexible magnetic pad 16 would be relatively thicker, i.e., about 3 mm.

The number of individual transducers 13 or the size of the grid can be up to about one hundred transducers. Physical dimensions are chosen for the particular application or material to be measured, such as a relatively large reactor vessel, as well as taking into consideration ease of transportability of the thickness gage. The spacing of the grid would be dependent upon the amount of sensitivity required for the tests to be performed. The desired sensitivity of the device 10 is dependent upon how localized the corrosion/erosion is. More localized wall thinning can best be examined by transducers which are more closely spaced to form a smaller grid pattern for a more sensitive multi-point gage. Increasingly smaller sized meshes or grids can provide for a more exact measurement of an area identified as one in which more localized and/or rapid deterioration of the pipe wall is taking place. This can be accomplished, for example, by placing the same size pad having more transducers than the first over the location; the second grid pattern thus being smaller than the first. Or, a smaller pad having the same number of transducers as the first but more closely spaced with respect to each other, thus having a smaller or finer grid pattern, is placed over that area identified as having more localized wear.

In order to provide for more precise replicability of thickness measurements, the pad 16 is to be located on the pipe 19 using permanent markers such as punch holes 37. A permanent identifying symbol 40 for each location is permanently marked on the pipe 19. These permanent markings 40 are identifiable for each separate location 17, and provide an alignment means for the flexible pad 16 which is located by the punch hole marks 37 in the magnetic flexible pad 16. Since the pad 16 has a known geometry, it can be placed at the exact location years later. Each transducer 13 has a defined predetermined location with respect to the pad 16. Once the individual locations for the matrix of transducers 13 on the pad 16 are defined, only the individual locations 17 need to be identified for the particular structure to be measured. Typically, these locations may already be known for piping systems of existing power plants. Because of this higher degree of reliability through exact replicability of measurement for a given location, fewer inspections would be required at the same location. By being able to precisely relocate the magnetic pad 16 at the same location 17, a more accurate rate of wall thinning is possible. Since a grid need not be laid out and painted each time a reading is to be taken, the device has the potential to save a tremendous amount of time and cost for this type of inspection.

In order to perform the multi-point wall thickness measurement, the following steps preferably are performed:

The pipe 19 is permanently marked at the predetermined locations 17 at which testing is to be performed. Such markings would have an identifying symbol 40 for each location so that it can be readily identified and defined. After an appropriate couplant is applied to the contact face of each transducer, the flexible magnetic pad 16 having the ultrasonic transducers associated therewith is positioned over the predetermined location 17. The pad 16 is adapted to be aligned with respect to the permanent markings 40, such as by their being visually locatable through punch holes 37 in the pad. After the pad 16 has been accurately positioned, an ultrasonic signal is generated and simultaneously sent to each of the transducers and transmitted into the pipe wall 19. The ultrasonic signal is received back from the pipe wall 19 through the transducer 13 and each signal is simultaneously received by the receiver. The time it takes for the signal to be sent and received is converted into an indication of the pipe wall thickness and can be visually seen on the screen 26 of the receiver. The readings for each of the discrete points is retrievably stored in a conventional storage device, such as a computer, for later comparison with new readings.

The generated signals are compared with any previously stored values, which can be the initial pipe wall dimensions, to generate an output indicative of the rate of pipe wall thinning. These steps are periodically repeated to generate an accurate reading of the rate of pipe wall thinning over time. If any localized wall thinning is identified, a more sensitive grid of ultrasonic transducers can be placed over that particular area to provide a more detailed readout of the pipe wall at that location. After the readings have been taken for a particular location, the operator can move onto the next predetermined or identified location to perform the same steps there.

While specific embodiments of the invention have been described in detail, it will be appreciated by those skilled in the art that various modifications and alterations would be developed in light of the overall teachings of the disclosure. Accordingly, the particular arrangements disclosed are meant to be illustrative only and not limiting as to the scope of the invention which is to be given the full breadth of the appended claims and in any and all equivalents thereof.

I claim:

1. An apparatus for simultaneously measuring the thickness of a ferro-magnetic material at a plurality of discrete points, the measuring apparatus comprising:
   a magnetic pad securable to said ferro-magnetic material at a predetermined location;
   a plurality of individual ultrasonic transducers associated with the magnetic pad so as to form a grid pattern for measuring the thickness of the material at each of said discrete points;
   means for transmitting an ultrasonic pulse through each of said transducers and into the ferro-magnetic material; and
   means for receiving a plurality of return signals from the ferro-magnetic material, one signal through each of said transducers, said return signals being indicative of the thickness of the material at each of said discrete points.

2. The apparatus as in claim 1, further including a means for displaying the value of said return signals indicative of thickness.

3. The apparatus as in claim 1, further including a means for retrievably storing said return signals.

4. The apparatus as in claim 1, wherein said transducers are biased in a direction towards the ferro-magnetic material.

5. An apparatus for simultaneously measuring the wall thickness of a carbon steel pipe at a plurality of discrete points, the measuring apparatus comprising:
   a flexible pad magnetically securable to the pipe at a predetermined location;
   a plurality of individual ultrasonic transducers associated with the flexible pad so as to form a matrix for measuring the wall thickness of the pipe at each of said discrete points;

means for transmitting an ultrasonic pulse through each of said transducers and into the pipe wall; and means for receiving a plurality of corresponding return signals from the pipe wall, one signal through each of said transducers, said return signals being indicative of the wall thickness of the pipe at each of said discrete points.

6. The apparatus as in claim 5, further including a means for displaying the value of said return signals indicative of the pipe wall thickness.

7. The apparatus as in claim 5, further including a means for retrievably storing said return signals.

8. The apparatus as in claim 5, further including an alignment means for precisely attaching the flexible pad on the predetermined location of the pipe.

9. The apparatus as in claim 8, wherein the alignment means is comprised of one or more permanent marks on the pipe locatable with respect to the flexible pad so as to provide precise alignment therebetween.

10. The apparatus as in claim 9, wherein said transducers are biased in a direction towards the pipe.

11. A multi-point wall thickness gage for simultaneously measuring the wall thickness of a carbon steel ferro-magnetic pipe at a plurality of discrete points, the thickness gage comprising:

a flexible magnetic pad securable to the pipe at a predetermined location;

a plurality of individual ultrasonic transducers associated with the flexible magnetic pad so as to form a matrix for measuring the wall thickness of the pipe at each of said discrete points;

means for simultaneously transmitting an ultrasonic pulse to each of said transducers and into the pipe wall;

means for simultaneously receiving a plurality of corresponding return signals from the pipe wall, one signal through each of said transducers, said return signals being indicative of the wall thickness of the pipe at each of said discrete points;

means for displaying the value of said return signals indicative of the pipe wall thickness; and means for retrievably storing said return signals.

12. The thickness gage as in claim 11, further including an alignment means wherein the predetermined location of the pipe is locatable by way of the flexible pad for precisely aligning the flexible pad thereon.

13. The thickness gage as in claim 12, wherein said transducers project through the magnetic pad and are biased in a direction towards the pipe.

14. The thickness gage as in claim 12, wherein said transducers are positioned a predetermined distance from the pipe.

15. A method of simultaneously monitoring the rate of wall thinning of a carbon steel ferro-magnetic object at a plurality of discrete points, the method comprising the steps of:

(i) permanently marking the ferro-magnetic object at one or more predetermined locations;

(ii) positioning a flexible magnetic pad having a plurality of individual ultrasonic transducers arranged in a grid pattern thereon at said predetermined location, the pad being adapted to be aligned with respect to said permanent markings;

(iii) generating a plurality of ultrasonic signals indicative of the object wall thickness at each of said discrete points through said ultrasonic transducers;

(iv) retrievably storing said generated signals;

(v) comparing said generated signals with previously stored values to generate and output indicative of object wall thinning; and (vi) subsequently repeating steps (ii) through (v) to generate a second output indicative of the rate of object wall thinning over time.

16. The method as recited in claim 15, including the steps of displaying said signals indicative of the wall thickness of the object, displaying the output indicative of wall thinning of the object, and displaying the second output indicative of the object wall thinning over time for each of said discrete points.

17. The method as recited in claim 15, further including the step of placing a second flexible magnetic pad having a plurality of ultrasonic transducers arranged in a second grid pattern smaller than the first thereon at said predetermined location.

18. A method of simultaneously monitoring the rate of wall thinning of a carbon steel ferro-magnetic pipe at a plurality of discrete points, the method comprising the steps of:

(i) permanently marking the ferro-magnetic pipe at one or more predetermined locations;

(ii) positioning a flexible pad having a plurality of ultrasonic transducers arranged in a grid pattern thereon at said predetermined location, the pad being adapted to be aligned with respect to said permanent markings;

(iii) generating a plurality of ultrasonic signals indicative of the pipe wall thickness at each of said discrete points through said ultrasonic transducers;

(iv) retrievably storing said generated signals;

(v) comparing said generated signals with previously stored values to generate and output indicative of pipe wall thinning;

(vi) subsequently repeating steps (ii) through (v) to generate a second output indicative of the rate of pipe wall thinning over time; and (vii) placing a second flexible pad having a plurality of ultrasonic transducers arranged in a second grid pattern smaller than the first thereon at said predetermined location.

19. The method as recited in claim 18, including the steps of displaying said signals indicative of the wall thickness of the pipe, displaying the output indicative of wall thinning of the pipe, and displaying the second output indicative of the pipe wall thinning over time for each of said discrete points.

* * * * *